United States Patent [19]

Ferrari

[11] Patent Number: 4,569,353
[45] Date of Patent: Feb. 11, 1986

[54] SOUND ATTENUATION MEASUREMENT SYSTEM

[75] Inventor: Leonard A. Ferrari, San Clemente, Calif.

[73] Assignee: The Regents of the University of California, Berkeley, Calif.

[21] Appl. No.: 384,554

[22] Filed: Jun. 3, 1982

[51] Int. Cl.⁴ ............................................. A61B 10/00
[52] U.S. Cl. ..................................... 128/660; 73/599
[58] Field of Search ................... 128/660, 661; 73/599

[56] References Cited

U.S. PATENT DOCUMENTS 4,389,893  6/1983  Ophir et al. ...................... 128/660 X
4,441,368  4/1984  Flax ................................. 128/660 X
4,452,085  6/1984  Pelc et al. ........................ 128/660 X Primary Examiner—Kyle L. Howell
Assistant Examiner—Francis J. Jaworski
Attorney, Agent, or Firm—Poms, Smith, Lande & Rose

[57] ABSTRACT

A system determines the attenuation of sound in a media supporting acoustic pulse propogation. The system includes a pulse circuit generating a reference pulse, which is then transformed into an ultrasonic acoustic pressure signal by a transducer. The transducer projects the pressure signal against the media and receives acoustic pressure signals reflected therefrom in response to the projected signal. A delay circuit, coupled to the pulse circuit generates a delayed pulse with an adjustable delay relative to the reference pulse. The duration of the delayed pulse defines a reference frame to examine reflected acoustic pressure signals reflected from a depth in the media defined by the delay of the pulse. A frequency circuit counts the number of zero crossings in the reflected acoustic pressure signal during the interval defined by the duration of the delayed pulse and determines the mean frequency of those reflections at the depth defined by the delay. The attenuation is proportional to the slope of a line fit to an arbitrary number of mean frequencies plotted against the depths corresponding thereto.

7 Claims, 7 Drawing Figures

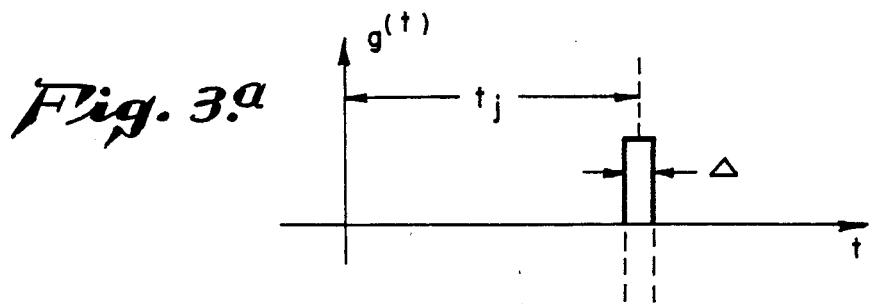
Fig. 3.a
Fig. 3.b
Fig. 3.c
Fig. 5.
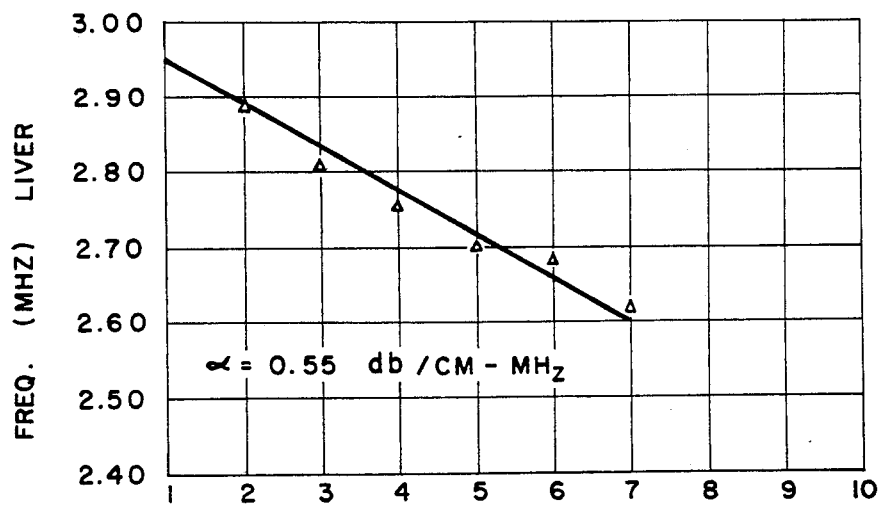

SOUND ATTENUATION MEASUREMENT SYSTEM

FIELD OF THE INVENTION

The present invention relates to the determination of the attenuation of sound in media supporting acoustic pulse propagation.

BACKGROUND OF THE INVENTION

The attenuation of sound in tissue is strongly frequency dependent, is a major acoustical property of tissue, and is a useful parameter for tissue characterization schemes. Research has shown that normal liver, pancreas, and spleen tissue can be differentiated on the basis of their frequency dependent attenuations and that cirrhotic liver tissue has almost twice the attenuation of normal liver tissue. It is also well known that malignant tumors are more highly attenuating than benign tumors which, in turn, are more attenuating than normal tissue. Moreover, normal, infarcted and ischemic heart tissue can be differentiated by measurements of frequency dependent attenuation.

The prior art does not teach any simple method or apparatus for the in vivo measurement of attenuation.

Accordingly, it is the principal object of the present invention to obtain accurate in vivo measurements of attenuation.

It is a further object of the present invention to measure in vivo attenuation simply and reliably.

Yet another object of the present invention is to utilize the frequency dependent nature of sound attenuation to determine sound attenuation.

SUMMARY OF THE INVENTION

The present invention, in a broad aspect, provides a system for determining the attenuation of sound in media supporting acoustic pulse propagation. A pulse circuit in the system generates a reference pulse. A transducer, coupled to the pulse circuit, transforms the reference pulse into an ultrasonic acoustic pressure signal and then projects the signal against the media and receives acoustic pressure signals reflected from the media in response to the projected signal. A delay circuit, coupled to the pulse circuit, generates a delay pulse, adjustably delayed relative to the reference pulse, with the duration of the delayed pulse defining a reference frame to examine reflected acoustic pressure signals reflected from a depth in the media defined by the delay. A frequency circuit, coupled to the transducer, measures the number of zero crossings in the reflected acoustic pressure signal during the time interval defined by the duration of the delayed pulse. Hence, the frequency circuit determines the mean frequency of the reflected acoustic pressure signal at this depth from the number of zero crossings and the time interval. The mean frequency is computed by dividing the number of positive or negative going zero crossings by the time interval. The attenuation is proportional to the slope of a line fit to an arbitrary number of mean frequencies plotted against the depths corresponding thereto as defined by the delay.

In accordance with one feature of the invention, the frequency circuit can include a frequency counter having a frequency input and a gate input with the gate input enabling the counter to count events at the frequency input. The delayed pulse is coupled to the gate terminal, while the reflected acoustic pressure signal is coupled to the frequency input terminal. The frequency counter thereupon counts the number of zero crossings during the duration of the delayed pulse and computes the mean frequency. The mean frequency is computed by dividing the number of positive- and negative-going zero crossings by the time interval.

In accordance with another feature of the invention, a gate circuit coupled to the delay circuit is used to transform the delayed pulse into a rectangular pulse. A driver circuit, coupled between the pulse circuit and the transducer, raises the level of the reference pulse to a level to drive the transducer. An amplifier, coupled between the transducer and the frequency circuit amplifies the level of the reflected acoustic pressure signal.

In accordance with yet another feature of the invention, a method for determining the attenuation of sound in a media supporting acoustic propagation includes the steps of generating a reference pulse, transforming the reference pulse into an ultrasonic pressure signal, projecting the acoustic pressure signal against the media and receiving reflected acoustic pressure signals therefrom. Simultaneously, an adjustable delay pulse is generated which defines a reference frame to examine the reflected acoustic pressure signals reflected from a depth in the media defined by the delay. Thereafter, the mean frequency of the reflected acoustic pressure signal during the duration of the delay pulse is computed. The mean frequency corresponds to the depth defined by the delay. A graph is then plotted of a number of these mean frequencies against the depths corresponding thereto and the slope of the graph is determined. The slope is proportional to the attenuation.

Other objects, features, and advantages of the present invention will become apparent from a consideration of the following detailed description and the accompanying drawings.

BRIEF DESCRIPTION OF THE DRAWINGS

FIGS. 3a, 3b and 3d show waveforms of the circuit in FIG. 2;

FIG. 5 shows a graph of the mean frequency relative to the depth of the media, with the slope to which the sound attenuation is proportional computed therefrom.

DETAILED DESCRIPTION

A. Theoretical Background

The present invention determines the attenuation $\alpha$ in db/cm MHz of a medium supporting acoustic pulse propagation by measuring the frequency shift in the acoustic echo signals or "A-lines" resulting from an acoustic pulse projected against the medium.

The present invention is based on the fact that a pulse subjected to frequency dependent attenuation still retains its basic shape, shifting only its center frequency and bandwidth. Accordingly, the shift in the center frequency of the pulse can be mathematically related to the attenuation by the expression $\alpha = k\nu$, where $\nu$ is the center frequency shift caused by the attenuation. By measuring the mean frequency of the reflected waveform in a window which is moved in depth, an estimate of the attenuation can be obtained. As set forth below, this can be accomplished in hardware by passing gated rf A-line waveform through a frequency counter which counts zero crossings of the wave form in the window and computes frequency. This method of determining the attenuation is unaffected by intervening media such as other tissue and is generally independent of the geometry and nature of reflecting structures.

Regarding an exact mathematical expression for $\alpha$, the attenuation versus frequency characteristic $H(\nu)$, of a linear attenuating medium has the form $H(\nu) = \exp[-k\nu r]$. For such a medium, the center frequency shift of a gaussian modulated pulse introduced by propagation through a distance r is given by the following equation:

$$\Delta\nu_p = \nu_{p1} - \nu_{po} = 0.18k\nu^2_{po}rB^2/\nu^2_{po} = 0.18krB^2 \quad (1)$$

where B is the 6 db transducer bandwidth.

The dimensions of k are nepers/cm-MHz. The usual attenuation coefficient, $\alpha$, with dimension db/cm-MHz is given in terms of k by the equation:

$$\alpha = (20 \log_{10} e)k \, db/cm\text{-}MHz$$

$$k = (0.1151)\alpha$$

Substitution into equation (1) above yields the following equation:

$$\alpha = [(48.27)\Delta\nu_p/B^2 r] db/cm\text{-}MHz \quad (2)$$

Figure 1:
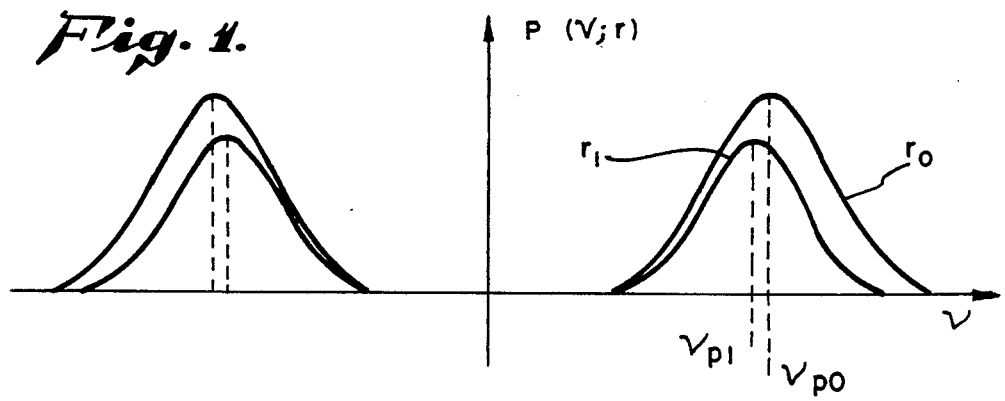
FIG. 1 illustrates pulse spectral shift in a media due to linear attenuation.

The computation of $\alpha$ from A-line data is done as follows. Given $P(\nu; t_0)$, the initial pulse spectrum and $P(\nu; t_1)$, the pulse spectrum after propagating a round trip distance $R_1$ in the medium, as illustrated in FIG. 1, an exact expression for the frequency shift of a gaussian modulated pulse is given by equation (1) above.

In the case of a gaussian modulated pulse, the mean frequency of spectrum is the modulation frequency. This frequency can be measured by a gated counter by measuring the time between zero crossings of the modulated pulse.

B. The Apparatus

Figure 2:
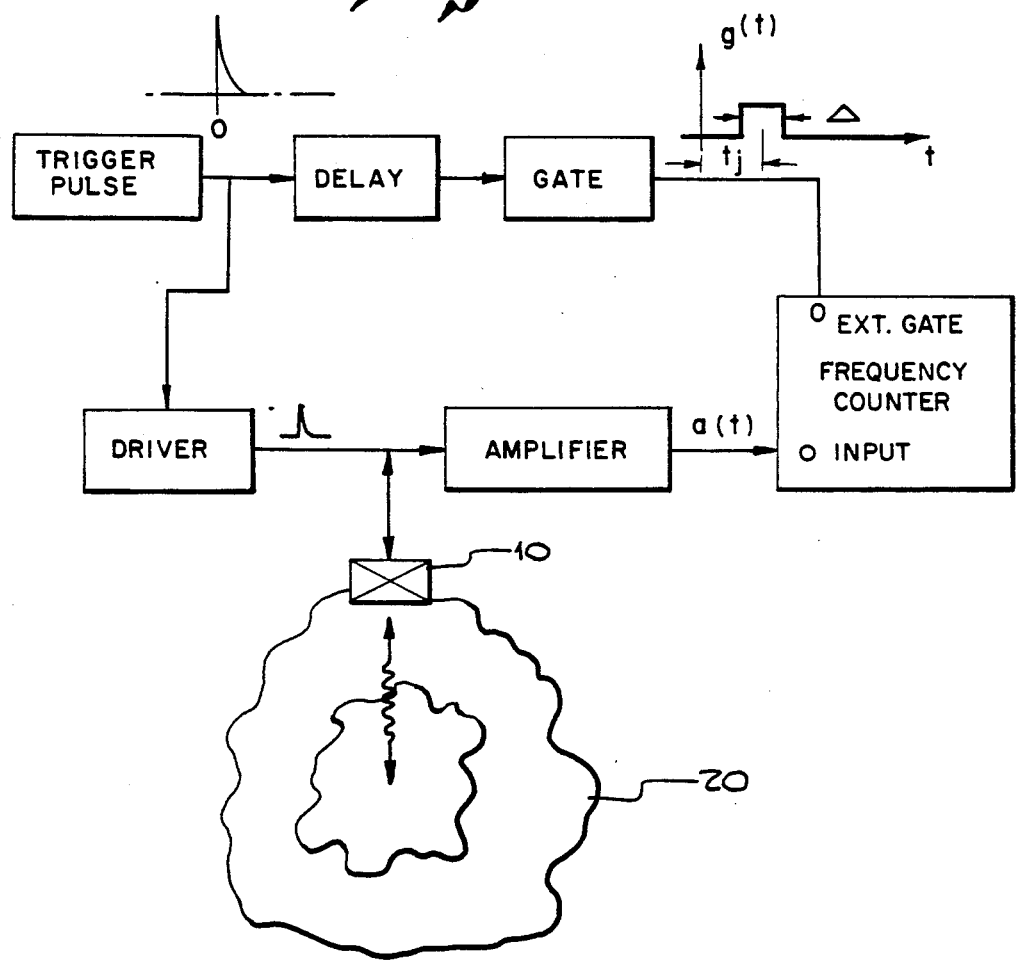
FIG. 2 shows a schematic diagram of a system, according to the present invention, for measuring sound attenuation in the media.

FIG. 2 shows a system, according to the present invention, which uses time gating to measure the average frequency in the time interval $[t_j - \Delta/2, t_j + \Delta/2]$ in an A-line, $A_i(t)$. Ths average or mean frequency corresponds to the RMS frequency of the power spectrum of the random process generated by the echos of the pulse propagating in the medium.

The components in FIG. 2 are conventional and have only been shown in block diagram form. Basically, the system of FIG. 2 includes a trigger pulse circuit which generates a reference pulse. This reference pulse is coupled to a driver circuit which then raises the voltage and current levels of the pulse. Coupled to the driver circuit is a transducer 10 which transforms the reference pulse into an ultrasonic acoustic pressure signal, which projects the acoustic pressure signal against the media supporting acoustic pulse propagation 20. The transducer also receives acoustic pressure signals reflected from the media. The reflected acoustic pressure signals are amplified by an amplifier and passed to a frequency counter.

Contemporaneous with the transmission of the ultrasonic acoustic pressure signal, a delay circuit, coupled to the pulse circuit, generates a delayed pulse with an adjustable delay relative to the reference or trigger pulse. In FIG. 2, the delay is given the abbreviation $t_j$. The delayed pulse is passed through a gate which makes the pulse rectangular and establishes a duration $\Delta$ for the pulse. The gate pulse, shown as g(t) in FIG. 2, is used to control an external gate of the frequency counter. The frequency counter has its frequency input coupled to the amplifier circuit. The frequency counter measures the number of zero crossings in the reflected waveform a(t) during the time interval established by the delayed pulse and then computes the average frequency of the reflected acoustic pressure signal during that time interval. This process is shown more clearly in FIG. 3. FIG. 3a shows the delayed pulse with pulse duration $\Delta$. FIG. 3b shows the waveform a(t) containing reflections from various depths in the media. FIG. 3c is an expanded version of a(t) in FIG. 3b during the interval $\Delta$ in FIG. 3a. The frequency counter in FIG. 2 thus determines the mean frequency of the reflected acoustic pressure signals during the interval $\Delta$.

As mentioned, the time delay $t_j$ defines a reference frame or "window" in which to examine reflected acoustic pressure signals from a particular depth. The particular depth r defined by the delay $t_j$ is given by the relationship $r = ct$, where c is the average media velocity of sound, generally on the order of 1500 meters per second for soft tissue. The time is, therefore, a good approximation of the depth. The depth of the window is increased by increasing the time delay. The limit on the time delay $t_j$ is that it must correspond to a distance within the depth of the tissue or organ being examined.

The parameter $\Delta$ is not particularly critical. If it is too long, however, the resolution will be inadequate. By contrast, if it is too short, there will not be enough zero crossings to accurately determine the mean frequency.

Figure 4:
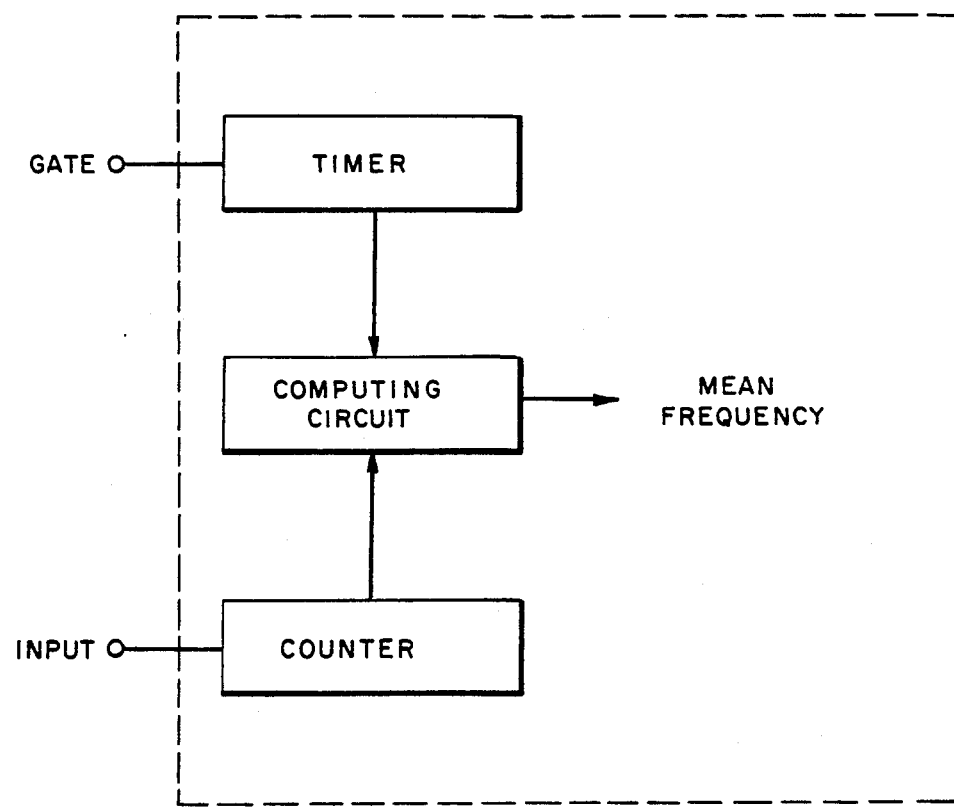
FIG. 4 shows an alternate embodiment of the frequency counter shown in FIG. 2.

FIG. 4 shows an alternate embodiment to the frequency counter shown in FIG. 3. In this embodiment, means are provided for accurantely measuring the duration $\Delta$ of the delayed pulse. This, for example, could be a high frequency clock. Separate means are also provided for counting the zero crossings in the reflected signal. The number of zero crossings are then divided by the time duration in a counting circuit to determine the mean reflected frequency.

Relative motion of the transducer relative to the medium effects averaging over a large number of different A-lines, e.g., $a_1(t), a_2(t), \ldots a_n(t)$. This produces the average frequency $\nu_a(t_j)$. By varying the location of the gate interval it is possible to obtain a plot of $\nu_a(t)$ versus t. Such a plot is shown in FIG. 5.

In many instances, $\Delta\nu_a$ is approximately equal to $\Delta\nu_p$ as indicated by the following equation:

$$\Delta\nu_p = \nu_{p1} - \nu_{po} \approx \nu_a(t_1) - \nu_a(t_o) = \Delta\nu_a$$

$\Delta\nu_a$ in the foregoing equation corresponds to the frequency shift of a random process, which is approximately the same as the pulse shift. The reason for obtaining the mean frequency of the A-line data is to eliminate noise and thus obtain better estimates of the various frequency shifts.

Having obtained $\Delta\nu_a$, it is then possible to use A-line data and equation (2), substituting $\Delta\nu_a$ for $\Delta\nu_p$ to obtain the attenuation coefficient.

C. Experimental Results

FIG. 5 shows the determination of the sound coefficient $\alpha$ for a liver obtained with the apparatus of the present invention. FIG. 5 shows $\nu_a(t)$ versus t for in vivo lateral human liver measurements. For FIG. 5, the Δ value was 20 microseconds, and $v_a(t_j)$ was averaged over $10^5$ zero crossings. All of the gate time locations ($t_j$) were located within the liver. The mean frequencies of the reflected signals were then plotted against time and a slope of the line of 0.058 MHz/div was obtained. The value of α was then computed with the following formula:

$$\alpha = \frac{(48.27)(.058) \text{ db} - \text{MHz}}{(1.3 \text{ MHz})^2 (20 \text{ }\mu s)(.15 \text{ cm}/\mu s)} = 0.55 \text{ db/cm} - \text{MHz}$$

The foregoing equation is equation (2), where 1.3 MHz is the transducer bandwidth, and where r is computed as discussed previously. The value of 0.55 db/cm-MHz compares very favorably with established values.

It should be noted that the graph shown in FIG. 5 was generated using a linear least squares fit of the data. Other data fitting techniques could also be used to obtain the necessary line slope to compute the attenuation.

As seen from the foregoing, the present invention not only sets forth a novel apparatus, but a novel method for computing the attenuation.

From the foregoing description of the present invention, a preferred embodiment of the invention has been set forth. It is to be understood that other mechanical and design variations are within the scope of the present invention. Accordingly, the present invention is not limited to the particular arrangement which has been described and illustrated herein.

What is claimed is:

1. A system for determining attenuation of sound in a media supporting acoustic pulse propagation, comprising:
    pulse circuit means for generating a reference pulse;
    transducer means, coupled to said pulse circuit means, for transforming said reference pulse into an ultrasonic acoustic pressure signal, for projecting said signal against said media, and for receiving acoustic pressure signals reflected from said media in response to said projected signal;
    delay circuit means, coupled to said pulse circuit means, for generating a delayed pulse with an adjustable delay relative to said reference pulse, the duration of said delayed pulse defining a reference frame to examine reflected acoustic pressure signals reflected from a depth in said media defined by said delay; and
    frequency circuit means, coupled to said transducer means, for measuring the number of zero voltage crossings in said reflected acoustic pressure signals during the time interval defined by the duration of said delayed pulse, and for determining the mean frequency of said reflected acoustic pressure signals at said depth from said number of zero crossings and said time interval, said attenuation being proportional to the slope of a line fit to an arbitrary number of said mean frequencies plotted against the depths corresponding thereto as defined by said delays.

2. A system as defined in claim 1, wherein said system further includes:
    gate circuit means, coupled to said delay circuit means, for transforming said delayed pulse to a rectangular pulse;
    driver circuit means, coupled to said pulse circuit means and said transducer means, for raising the level of said reference pulse to a level to drive said transducer means; and
    amplifier means, coupled between said transducer means in said frequency circuit means, for amplifying the level of said reflected acoustic pressure signal.

3. A system as defined in claim 1, wherein:
    said frequency circuit means comprises a frequency counter having a frequency input terminal and a gate input terminal, with said gate input terminal enabling said counter to count events at said frequency input terminal and to determine the frequency thereof;
    said delayed pulse is coupled to said gate input terminal; and
    said reflected acoustic pressure signal is coupled to said frequency input terminal, whereupon said frequency counter counts the number of said zero crossings during the interval of said delayed pulse and computes said mean frequency.

4. A system as defined in claim 1, wherein said frequency circuit means comprises:
    counter means, coupled to said transducer means, for counting said number of zero crossings;
    timer circuit means, coupled to said delay circuit means, for measuring the duration of said delayed pulse; and
    computing circuit means, coupled to said counting means and to said timer circuit means, for dividing the number of said zero crossings as counted by said counter means by the duration of said delayed pulse as measured by said timer circuit means to determine said mean frequency.

5. A method for determining the attenuation of sound in a media supporting acoustic pulse propagation, comprising:
    generating a reference pulse;
    transforming said reference pulse into an acoustic pressure signal;
    projecting said acoustic pressure signal against said media;
    receiving acoustic pressure signals reflected from said media;
    generating a delay pulse having an adjustable delay relative to said reference pulse to define a reference frame to examine said reflected acoustic pressure signals reflected from a depth in said media defined by said delay;
    determining the mean frequency of said reflected acoustic pressure signals during the duration of said delayed pulse, said mean frequency corresponding to the depth defined by said delay;
    plotting a graph of a number of said mean frequencies against the depths corresponding thereto; and
    determining the slope of said graph, said attenuation being proportional to said slope.

6. A method as defined in claim 5, wherein said step of determining said mean frequency comprises the steps of:
    measuring the time duration of said delayed pulse;
    counting the number of said zero crossings; and
    dividing said number by said time to obtain said mean frequency.

7. A method as defined in claim 5, wherein said step of plotting said graph comprises:
    determining said mean frequency for an arbitrary number of said depths;
    graphically plotting the mean frequency determined at each of said depths; and
    fitting a line to said plot.

* * * * *